(12) United States Patent
Haberer et al.

(10) Patent No.: US 6,677,597 B1
(45) Date of Patent: Jan. 13, 2004

(54) DEVICE AND METHOD FOR CONTROLLING A RASTER SCANNER IN ION-BEAM THERAPY

(75) Inventors: Thomas Haberer, Darmstadt (DE); Wolfgang Ott, Darmstadt (DE)

(73) Assignee: Gesellschaft fuer Schwerionenforschung mbH, Darmstadt (DE)

( * ) Notice: Subject to any disclaimer, the term of this patent is extended or adjusted under 35 U.S.C. 154(b) by 0 days.

(21) Appl. No.: 09/719,124

(22) PCT Filed: Mar. 27, 2000

(86) PCT No.: PCT/EP00/02689

§ 371 (c)(1), (2), (4) Date: Mar. 2, 2001

(87) PCT Pub. No.: WO00/62307

PCT Pub. Date: Oct. 19, 2000

(30) Foreign Application Priority Data

Apr. 12, 1999 (EP) .............................................. 99107121

(51) Int. Cl.[7] ........................ G01N 23/00; G01J 00/00; H05H 7/00; A61H 5/00

(52) U.S. Cl. ............................... 250/491.1; 250/370.1; 250/370.09; 315/500; 315/507; 315/501; 315/502; 601/15

(58) Field of Search ......................... 250/491.1, 370.09, 250/370.1; 601/15; 315/500, 507, 501, 502

(56) References Cited

U.S. PATENT DOCUMENTS

| 3,867,583 | A | * | 2/1975 | Dorazio et al. | ............. 340/2.24 |
| 3,965,434 | A | * | 6/1976 | Helgesson | ................... 315/500 |
| 4,477,882 | A | * | 10/1984 | Schumacher et al. | ........ 709/251 |
| 4,667,111 | A | * | 5/1987 | Glavish et al. | ........... 250/492.2 |
| 4,713,581 | A | * | 12/1987 | Haimson | .................... 315/5.41 |
| 4,982,320 | A | * | 1/1991 | Eaton et al. | ................... 700/45 |
| 5,017,789 | A | * | 5/1991 | Young et al. | ......... 250/396 ML |
| 5,260,581 | A | * | 11/1993 | Lesyna et al. | ............. 250/492.3 |
| 5,298,867 | A | * | 3/1994 | Mestha | ......................... 315/500 |
| 5,898,279 | A | * | 4/1999 | Ezzedine et al. | ............ 315/502 |
| 6,509,573 | B1 | * | 1/2003 | Badura et al. | ............ 250/492.3 |

FOREIGN PATENT DOCUMENTS

| EP | 0 986 070 A1 | | 9/1998 |
| EP | 0986070 | * | 3/2000 |
| EP | 1085786 | * | 3/2001 |

* cited by examiner

*Primary Examiner*—John R. Lee
*Assistant Examiner*—K Fernandez
(74) *Attorney, Agent, or Firm*—Frommer Lawrence & Haug LLP; Ronald R. Santucci

(57) ABSTRACT

The invention relates to an apparatus and a method for the feedback control of a grid scanner in ion therapy. An apparatus of that kind for the feedback control of a grid scanner has scanner magnet current supply devices for ion beam scanner magnets that deflect horizontally and vertically with respect to the middle of the ion beam, the supply devices being controlled by control and read-out modules for the scanner magnets. Furthermore, the apparatus has a location-sensitive detector for location measurement, which is controlled by means of a control and read-out module. A sequence control device controls the activation and read-out sequence among the devices of the apparatus, the apparatus also having in the sequence control device a circuit arrangement having a feedback loop between the control and read-out modules for the scanner magnets and the control and read-out module of the location-sensitive detector. For that, the control and read-out modules for the scanner magnets and the control and read-out module of the location-sensitive detector in the sequence control device are technically so arranged, in circuitry and sequence, that the control and read-out modules for the scanner magnets are arranged serially after the control and read-out module of the location-sensitive detector.

10 Claims, 6 Drawing Sheets

DEVICE AND METHOD FOR CONTROLLING A RASTER SCANNER IN ION-BEAM THERAPY

BACKGROUND OF THE INVENTION

The invention relates to an apparatus and a method for the feedback control of a grid scanner in ion beam therapy, according to the preamble of claims 1 and 4.

The feedback control apparatus of that kind has, at least, the following devices:

scanner magnet current supply devices for ion beam scanner magnets that deflect horizontally and vertically with respect to the middle of the ion beam, the supply devices being controlled by control and read-out modules for the scanner magnets, a location-sensitive detector for location measurement, which is controlled by means of a control and read-out module, and a sequence control device, which controls the activation and read-out sequence among the devices of the apparatus.

A grid scanner of that kind is known from European Patent Application EP 98 117 256.2. That publication describes a grid scanning method with feedback control of intensity. Despite considerable variations in the intensity of the therapy beam, which consists of ions and varies in intensity by a factor of 30 between a maximum value and the average value, that method allows the specifications of an irradiation plan to be applied so precisely that the dose distribution resulting from the entire irradiation differs from the planned dose distribution by less than 5% on average. Feedback control of the intensity accordingly results in the fact that, despite the considerable variations in the intensity of an ion beam, it is possible to adhere very precisely to the total beam dose per beam position.

It is, however, problematic to achieve implementation of a geometrically exact application of the dose distribution, because not only the intensity of the therapy beam but also the beam position of the focussed therapy beam varies significantly during application of the beam. There is currently no complete and efficient solution to that problem. A huge amount of work is currently being expended on measuring those variations in position and drawing up correction tables for each conceivable accelerator and high-energy beam guidance setting—there are, for example, 255 energy stages each having 7 focussing stages and 15 intensity steps that have to be taken into account, so that about 25,000 combinations have to be measured for each beam position and correction tables have to be drawn up for corresponding therapy devices. Such correction tables can then be used to produce the control data for the system; but even that amount of work leads to a positive result only if the differences in the beam position are reproducible for each beam position, which cannot, however, generally be assumed to be the case.

The invention is therefore based on the problem of dramatically reducing the correction work and of significantly increasing the geometric precision.

SUMMARY OF THE INVENTION

An apparatus according to the invention for the feedback control of a grid scanner in ion beam therapy has, at least, the following devices:

scanner magnet current supply devices for ion beam scanner magnets that deflect horizontally and vertically with respect to the middle of the ion beam, the supply devices being controlled by control and read-out modules for the scanner magnets, a location-sensitive detector, which for location measurement is controlled by means of a control and read-out module, a sequence control device, which controls the activation and read-out sequence among the devices of the apparatus, wherein the apparatus also has in the sequence control device a circuit arrangement having a feedback loop between the control and read-out modules for the scanner magnets and the control and read-out module of the location-sensitive detector and wherein, in circuitry and sequence, the control and read-out modules for the scanner magnets and the control and read-out module of the location-sensitive detector in the sequence control device are technically so arranged that the control and read-out modules for the scanner magnets are arranged serially after the control and read-out module of the location-sensitive detector.

Apart from the quality of dose application, this apparatus also improves patient throughput and, as a result, the economical nature of the apparatus, because the increase in geometric precision reduces the number of interruptions in irradiation owing to interlocks of the location measurement system. Moreover, this solution benefits not only grid scan systems in fixed beam guides having any desired angle but also and especially the grid scan technique in combination with a rotatable beam guide (a gantry), wherein an increase in positional errors can be expected, because such gantry systems are extremely heavy and therefore have a tendency towards mechanical deformation of the beam guide.

Furthermore, the ion optics are very sensitive with respect to variations in position. Homogeneity of the magnetic field, especially in the final deflecting dipole magnet, is extremely difficult to produce, so that the present apparatus according to the invention for the feedback control of a grid scanner brings considerable advantages overall for such gantry systems, because the ion therapy beam in an irradiation position can be readjusted and realigned in accordance with an irradiation plan of the apparatus according to the invention.

In a preferred embodiment of the invention, a multi-wire proportional chamber is used as the location-sensitive detector. Such a detector has the advantage that, on the one hand, the actual state of the beam position can be accurately determined in its location co-ordinates and, on the other hand, as a result of the fact that the location-sensitive detector is coupled into a feedback control loop, the irradiation location can be matched to the irradiation plan and exact concordance between the actual value and desired value can be achieved with respect to the location of the irradiation.

For the purpose of simultaneous feedback control of intensity, the apparatus can preferably have at least one ionisation chamber, which co-operates with a control and read-out module. Preferably, that control and read-out module of the ionisation chamber is, within the sequence control, technically arranged, in circuitry and sequence, before the control and read-out module of the location-sensitive detector. That advantageously results in the fact that first of all the irradiation dose per beam position is monitored and adhered to by controlling the intensity and then, independently of the intensity control, precise positioning of the ion beam can additionally be feedback-controlled with the aid of the location-sensitive detector.

For the method for the feedback control of a grid scanner in ion beam therapy, the grid scanner has the following devices:
scanner magnet current supply devices for ion beam scanner magnets that deflect horizontally and vertically with respect to the middle of the ion beam, the supply devices being controlled by control and read-out modules for the scanner magnets,
a location-sensitive detector for location measurement, which is controlled by means of a control and read-out module, and
a sequence control device, which controls the activation and read-out sequence among the devices of the apparatus,
wherein the following method steps are performed:
comparison of information, deposited in the location measurement control and read-out module of a supervisory control system and relating to the desired position of the beam plan, with the actual measured position of the beam position from a location-sensitive detector, in real time,
determination of a correction value for the scanner magnet supply devices of the grid scanner, and
setting the correction value for the horizontal and vertical magnet supply devices of the grid scanner and realignment of the beam position.

An advantage of the method according to the invention lies in the fact that it is possible to dramatically reduce the measurement of a large number of system settings at the accelerator and/or the beam guide within the context of quality assurance and preparation of the irradiation unit for patient irradiation procedures, by using the location information from the position-sensitive detector before the patient for realignment of the beam position in real time during beam use. Moreover, as a result of this invention, the demands on reproducibility of the beam position are significantly relaxed for all high-energy radiation settings and the geometric precision of dose application improved.

For realignment of the beam position, the information deposited in the location measurement control and read-out module of the supervisory control system and relating to the desired position from the beam plan is compared in real time with the actual measured position from the location-sensitive detector and a correction value for the magnet supply devices of the grid scanner is determined and set. That correction can be made from measurement cycle to measurement cycle of the location measurement system, for example within 150 μs, or alternatively from one beam position in the irradiation plan to the next beam position. Within the real-time control of the system, a series of control and read-out modules are connected to one another by way of interfaces. Of relevance to the invention, however, are the two control and read-out modules that control and read out the location measurement detector and the two grid scanner magnet current supply devices.

For each measurement cycle, the real-time software in the control and read-out module of the location-sensitive detector calculates the actual value of the beam position from the detector raw data and sends that information to the control and read-out modules of the scanner magnets by way of the data connection. For each feedback control cycle, the real-time software in the control and read-out module of the scanner magnets compares the desired position and the actual position and calculates current-correction values for the horizontal and vertical magnet current supply device of the grid scanner and then sets the corrected current values, which result in improved magnetic field settings in the scanner magnets, as a result of which the beam position is improved.

In a preferred embodiment, beam realignment is carried out using damping that can be set by means of the real-time software in the control and read-out modules for the control magnets. As a result thereof, feedback control oscillations are advantageously avoided and carried-over errors are reduced.

In a further preferred embodiment, upper thresholds are fixed in order to limit location correction so that major errors in beam position settings are avoided for reasons of safety. Should such an upper threshold value be exceeded, rapid switching-off of the beam is preferably triggered by the control and trigger module of the location-sensitive detector in real time and, as a result, a chain of switch-off commands is triggered for the various accelerator and beam guidance components.

Further advantages, features and possible applications of the invention are described below in greater detail with reference to exemplary embodiments.

DETAILED DESCRIPTION OF THE INVENTION

Figure 1:
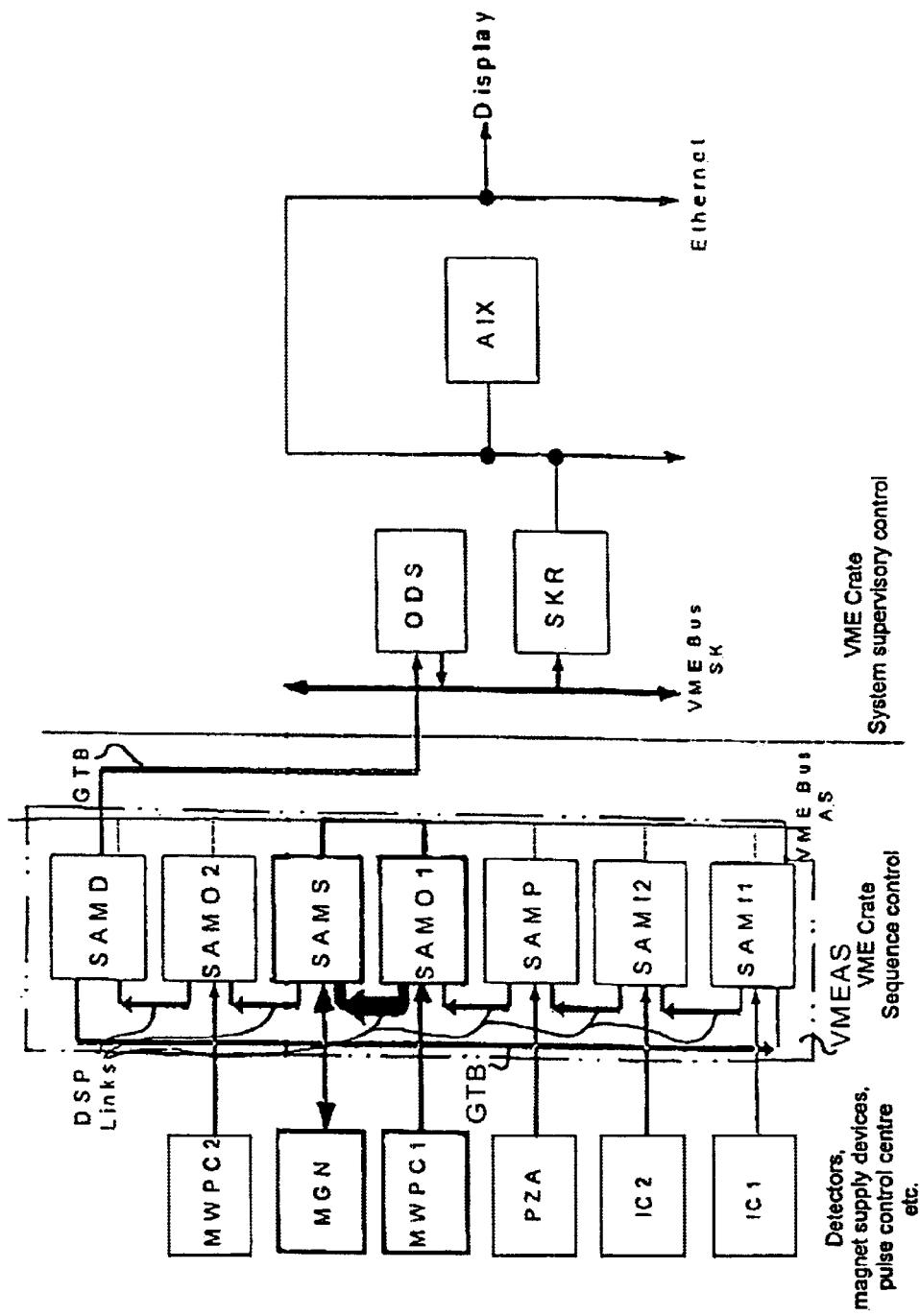
FIG. 1 shows a data flow plan for the feedback control of a grid scanner in a preferred embodiment of the invention.

FIG. 1 shows a data flow plan for the feedback control of a grid scanner in a preferred embodiment of the invention. The column at the far left of the data flow plan shows a selection of devices used for ion beam therapy, such as, preferably, detectors (IC1, IC2, MWPC1 and MWPC2), magnet supply devices (MGN) and pulse control centre activators (PZA). The second column from the left shows the data flow in a sequence control device (VMEAS) having control and read-out modules (SAM), which co-operate with the detectors, magnet supply devices and pulse control centre activators, the control and read-out modules (SAMI1 and SAMI2) co-operating with ionisation chambers (IC1 and IC2) for measurement of the ion beam particle number and, after an ion beam particle number prespecified by the treatment plan has been reached for a beam position, causing, by means of the control and read-out module (SAMP) for the pulse control centre activator (PZA), the ion beam to be switched over to the next beam position with the aid of the pulse control centre activator (PZA).

For the feedback control of a grid scanner in ion beam therapy in accordance with the invention, at least the following devices out of the devices and the control and read-out modules are necessary: a location-sensitive detector (MWPC1) for location measurement, which detector is controlled by means of a control and read-out module (SAMO1), scanner magnet current supply devices (MGN) for horizontal (X) and vertical (Y) deflection of the ion therapy beam from the middle of the ion beam by means of the scanner magnets, the supply devices (MGN) being controlled by control and read-out modules (SAMS) for the scanner magnets. A sequence control device (VMEAS) controls the activation and read-out sequence among the devices necessary for the apparatus according to the invention.

For that purpose, the data flow plan according to FIG. 1 shows a circuit arrangement in the sequence control device (VMEAS) having a feedback loop between the control and read-out modules (SAMS) for the scanner magnets and the control and read-out module (SAMO1) of the location-sensitive detector (MWPC1). For that feedback control loop, the control and read-out modules (SAMS) for the control magnets and the control and read-out module (SAMO1) of the location-sensitive detector (MWPC1) in the sequence control device (VMEAS) are technically so arranged, in sequence and circuitry, that the control and read-out modules (SAMS) for the scanner magnets are arranged serially after the control and read-out module (SAMO1) of the location-sensitive detector (MWPC1). The control and read-out modules (SAMS) for the scanner magnets and the control and read-out module (SAMO1) of the location-sensitive detector (MWPC1) consist of extremely fast microprocessors, which communicate with one another by way of corresponding digital-signal-processor links (DSP Links). The feedback loop between the control and read-out modules (SAMS) for the scanner magnets and the control and read-out module (SAMO1) of the location-sensitive detector is formed, on the one hand, by the digital-signal-processor links and a sequence control bus (VME-Bus-AS).

As a result of the serially downstream arrangement of the control and read-out modules (SAMS) for the horizontal (X) and vertical (Y) deflection of the control magnets, a real-time readjustment loop can advantageously be formed for on-line verification of position and correction of each beam position. In the case of a discrepancy in the actual position in an individual beam position out of 1,156 positions, as are present in the case of FIGS. 3a and 3b, or in the case of a discrepancy of an individual actual position with respect to a desired position out of the 2,116 planned beam positions of FIGS. 4a and 4b, the feedback control loop in accordance with the data flow plan of FIG. 1 intervenes and, in the case of real-time readjustment from beam position to beam position, corrects the beam position that follows next, as shown by FIG. 3b.

In the case of real-time readjustment from measurement cycle to measurement cycle, the real-time readjustment loop in accordance with the data flow plan according to FIG. 1 corrects and controls the position of the ion beam while still within the duration of a beam position, because the measurement cycle duration is shorter than a beam position duration. As a result, for each beam position, realignment of the actual position to the desired position of a treatment plan is brought about directly so that complete concordance of actual values with desired values is achieved, within predetermined limits, in accordance with FIG. 4b in the individual beam positions, in this case in the 2,116 beam positions.

In a preferred embodiment, a multi-wire proportional chamber is used as the location-sensitive detector (MWPC1). Such multi-wire proportional chambers have the advantage that it becomes possible to resolve, with millimetre precision, the location position of an ion beam in the ion beam therapy of this embodiment, for ion beams both of protons and of relatively heavy ions.

The uppermost microprocessor shown in FIG. 1 in the sequence control device (VMEAS) serves as a control and read-out module for online data transfer to the data store (ODS) in the adjacent system supervisory control shown on the right-hand half of the diagram of FIG. 1. That control and read-out module (SAMD) for online data transfer is connected to the data store (ODS) for online display by way of the device bus, which is a differential data bus between the control and read-out modules and their respective front-end electronics. In accordance with the data flow plan of FIG. 1, the data store (ODS) for online display sends its data by way of the bus of the system supervisory control (SK) and the system supervisory control computer in the bus system (VME) for connecting processors and data modules to the display, on the one hand, and to the Ethernet, on the other hand, under guidance of the operating system (AEX) in the system supervisory control.

In the embodiment according to FIG. 1, the feedback control system in ion beam therapy has at least one ionisation chamber (IC1), which serves for measuring the intensity of the ion beam and totals the ion beam particle number until the dose for a beam position has been reached so that a command can then be issued to the control and read-out module (SAMP) for the pulse control centre, which, by means of the pulse control centre activator (PZA), initiates switching over to the next beam position, which is then conveyed to the magnet current supply devices (MGN) of the grid scanner by way of the real-time readjustment loop. In a preferred embodiment of the invention, the control and read-out module (SAMI1) is, within the sequence control (VMEAS), technically arranged, in circuitry and sequence, before the control and read-out module (SAMO1) of the location-sensitive detector (MWPC1).

Figure 2:
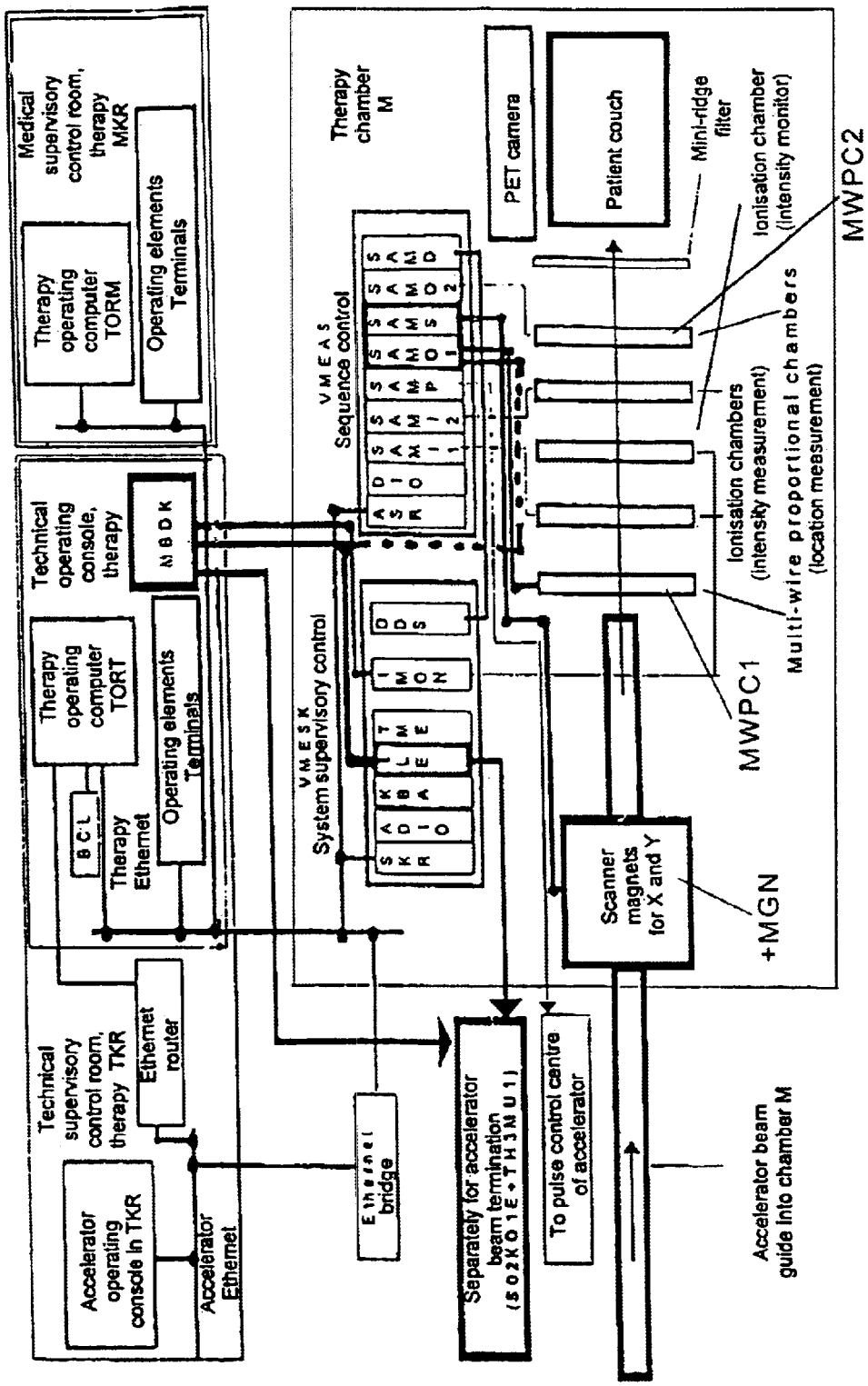
FIG. 2, in the form of a block circuit diagram, shows a preferred embodiment of the invention.

FIG. 2, in the form of a block circuit diagram, shows a preferred embodiment of the invention within a supervisory control system for an ion beam therapy unit. The supervisory control system for an ion beam therapy unit basically consists of a technical supervisory control room (TKR), in which all accelerator data on the Ethernet arrive at an accelerator operating console, and an Ethernet router sends data to the next larger unit of the supervisory control system for an ion beam therapy unit, the technical operating console in therapy itself. The central device of that technical operating console is the therapy operating computer (TORT), which has a barcode reader (BCL) and which is in communication with the operating element of the terminals by way of the therapy Ethernet. The technical operating console in the therapy area is provided with a medical operating console (MBDK), which is in communication with a therapy area (chamber M) and is provided with a direct connection for triggering termination of a beam of the accelerator, wherein for termination of the beam a resonance quadrupole (S02KQ1E) is set at zero for slow extraction of the beam by way of its supply device by means of an interlock unit in the bus system of the therapy supervisory control system and a deflection dipole magnet TH3MU1 of beam guidance to the therapy measurement location is likewise set at zero, in the case of a fault, for termination of the beam or extraction by means of the interlock unit (ILE) in the bus system (VME) of the therapy supervisory control system.

For the system supervisory control (VMESK) per se, a number of microprocessors co-operate on a bus system connection frame (VME-CRATE), to which there belongs, besides the data store (ODS) for online display previously mentioned and shown in FIG. 1, an intensity monitor (IMON), which co-operates inter alia with an ionisation chamber and the read-out electronics for monitoring the total particle number. In addition, a dead man's circuit unit (TME) is located in the system supervisory control for monitoring the functionality of the processors. Besides the interlock unit (ILE) previously mentioned and a supervisory control bus adapter (KBA), the system supervisory control is provided with an analogue-digital module (ADIO) and a system supervisory control computer (SKR) in the bus system (VME) of the system supervisory control.

The components of the sequence control (VMEAS) are identical to the components of the data flow plan shown in FIG. 1, the sequence control in the supervisory control system shown in FIG. 2 having, in addition, a digital input/output module (DIO) and a sequence control computer (ASR).

In the therapy area (chamber M) there is located a positron emitter tomograph (PET) for spatially determining the particle range by means of positron-emitting radiation, by means of which it is possible to detect the action of irradiation on a patient on the patient couch.

Guidance of the ion beam into the therapy area (chamber M) is shown in diagrammatic form in the lower portion of FIG. 2, the beam for local scanning being guided by scanner magnets for X and Y, which deflect the beam horizontally (X) and vertically (Y) with the aid of magnet current supply devices (MGN) of the grid scanner. After the beam has departed from the last deflection magnet (not shown), the beam is guided through a plurality of detectors before coming to the patient couch, wherein a feedback control loop, by way of a first location-sensitive detector (MWPCI), so acts on the magnet current supply devices (MGN) for the scanner magnets of the grid scanner that the beam position can be corrected by means of realignment from beam position to beam position or can be corrected while still within a single beam position by means of realignment from measurement cycle to measurement cycle.

Figure 3A:
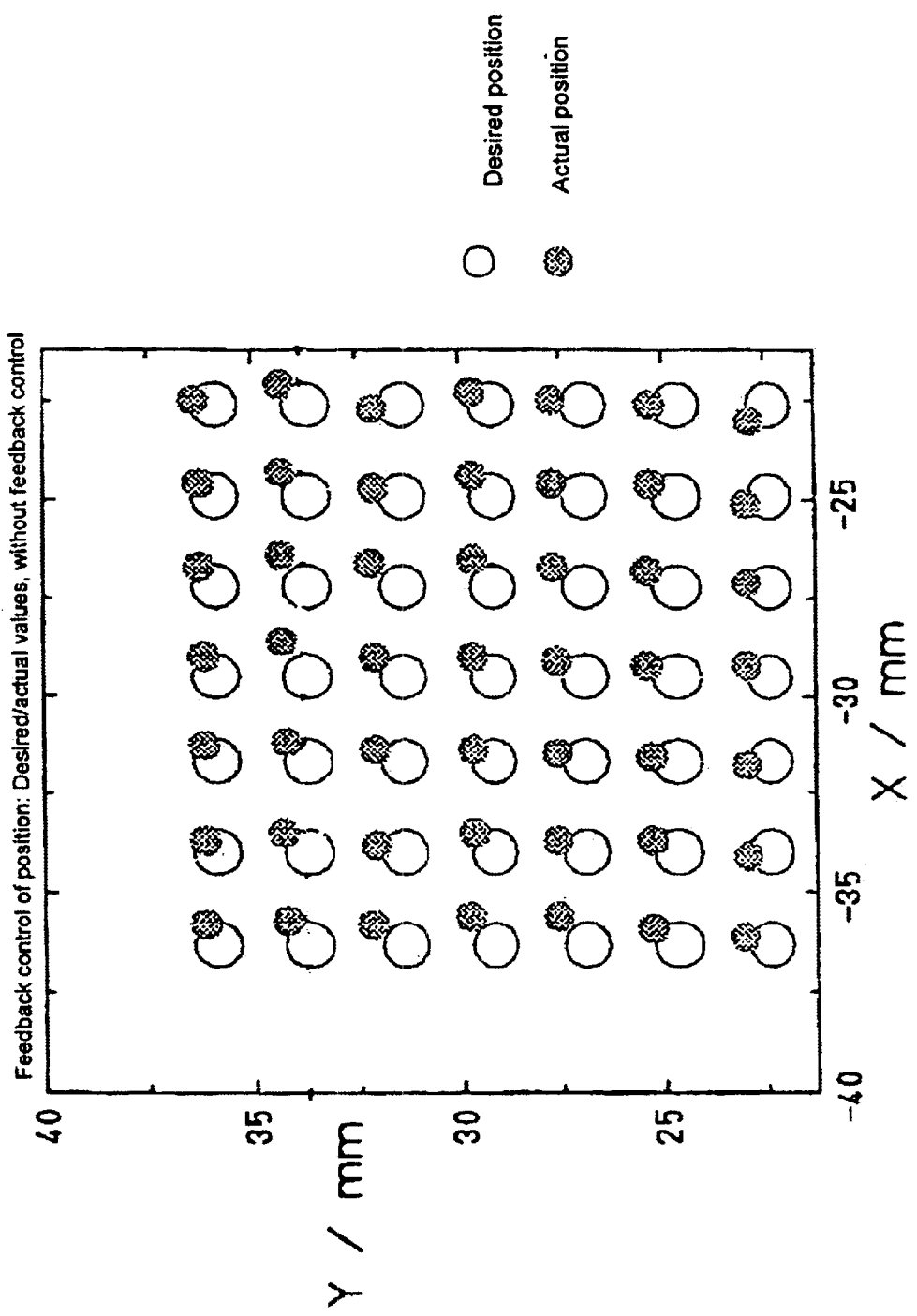
FIG. 3a shows a desired position/actual position comparison of an ion therapy beam of a grid scanner before switching on an apparatus according to the invention.
Figure 3B:
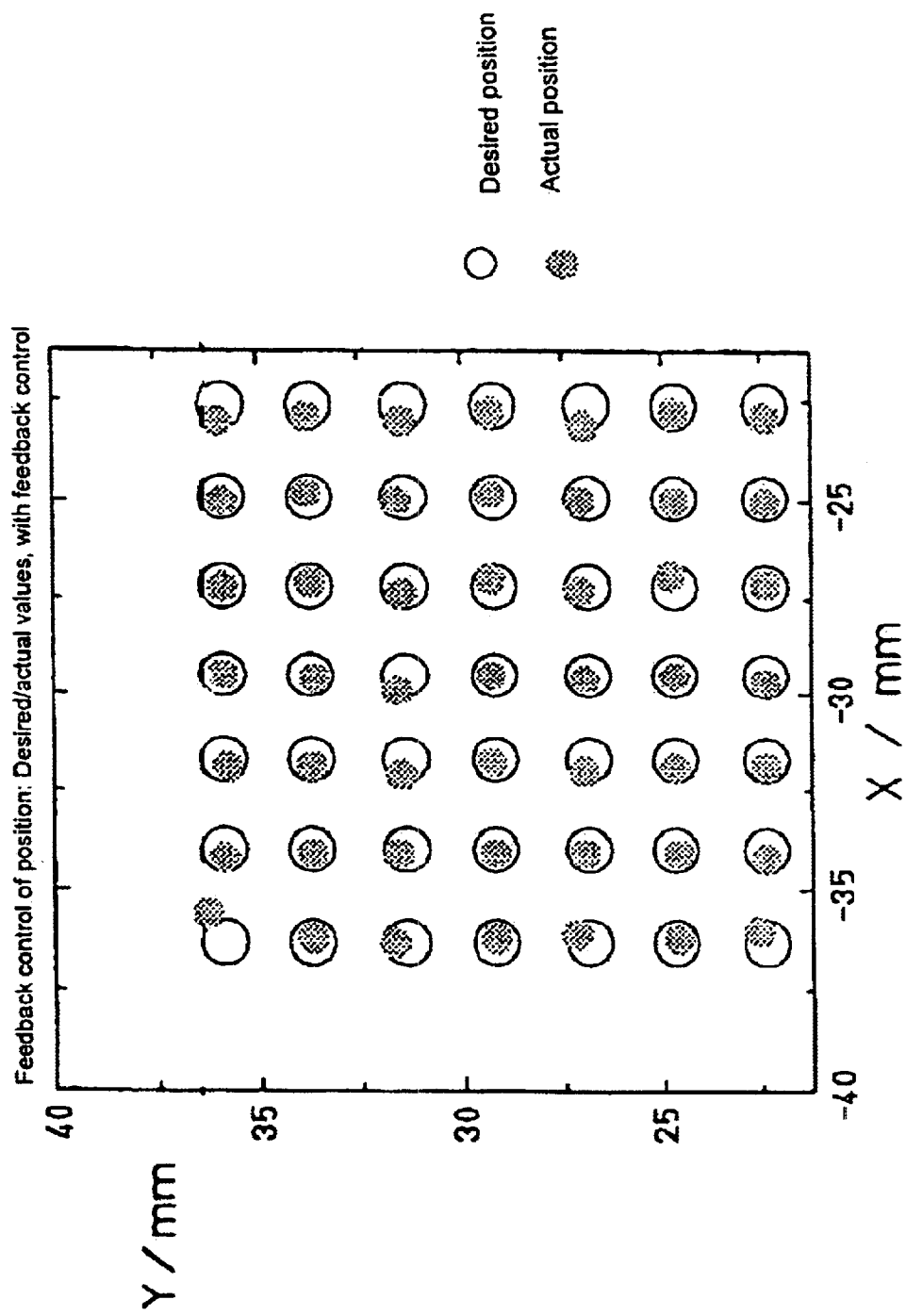
FIG. 3b shows a desired position/actual position comparison of FIG. 3a after switching on the apparatus for feedback control of the position from beam position to beam position of a grid scanner according to an embodiment of the invention.

FIG. 3a shows, for that purpose, a desired/actual position comparison of an ion therapy beam of a grid scanner before switching on an apparatus according to the invention, the position on the ordinate Y in that diagram being given in millimetres and the position on the abscissa X likewise being shown in millimetres. The reference point for those positional data is the isocentre at the origin of the co-ordinates, which in this case is located outside the 49 beam positions shown, an additional location-resolving detector (MWPC2) monitoring the concordance between the desired value and the actual value at the isocentre, that is to say at the origin of the co-ordinates.

It may accordingly be assumed that, up to a predetermined limit value, the desired valueslactual values at the isocentre are in concordance. Far away from the isocentre, as shown here, however, the actual values differ significantly from the desired values in the peripheral region of the planned irradiation. In the prior art, in order to overcome those discrepancies, hugely extensive correction tables have until now been drawn up by means of measuring and adjusting, and stored and retrieved individually during irradiation. In the case of a medical radiation requirement of 255 different energy stages each having 7 focussing stages and 15 intensity steps, that alone gives rise to 25,000 combinations per beam position. Distributed over the 1,156 beam positions given in the example of FIG. 3a, that results in a data set of more than 25,000,000. If the beam position is made denser, as in the example of FIG. 4a, over the 2,116 beam positions shown therein, that figure is doubled again to more than 50,000,000. The huge amount of work which has to be expended according to the prior art in order to measure such variations in position for all conceivable cases and to draw up correction tables which can be used to generate the control data for the system is avoided by the apparatus according to the invention and the method according to the invention for the feedback control of a grid scanner in ion beam therapy. That is especially so because the work in the prior art just mentioned and quantified, in which control is carried out by means of correction tables, only leads to the objective if the discrepancies are reproducible. Generally that cannot, however, be assumed to be the case, especially not with regard to the use of the grid scan technique in combination with a rotatable beam guide, such as a gantry.

FIG. 3b shows a desired value/actual value comparison of FIG. 3a after switching on the apparatus for positional feedback control from beam position to beam position according to an embodiment of the invention. As the result obtained by comparing the diagram in FIG. 3a and in FIG. 3b shows, after the discrepancy in the actual position with respect to the desired position has been detected in the beam position in the top left-hand corner, which is furthest away from the isocentre, excellent concordance between the actual position and the desired position is achieved for the next five beam positions. Only the actual position of the sixth beam position in the top row again differs significantly from the desired position; the third line then especially shows that, despite improvements with respect to FIG. 3a in actual positions compared to desired positions, there are nevertheless clearly visible departures from the planned desired position. In the fourth line, the feedback control from beam position to beam position results in very advantageous concordances between actual and desired positions whereas, in the other three lines also shown, only a significant improvement over the diagram in 3a is achieved, however, with congruent concordance between actual position and desired position being achieved only rarely. Overall, as a result of readjustment or realignment of the position of the ion therapy beam from planned desired position to planned desired position, a significant improvement is achieved in FIG. 3b compared to the control of FIG. 3a, which is matched only at the isocentre.

Figure 4A:
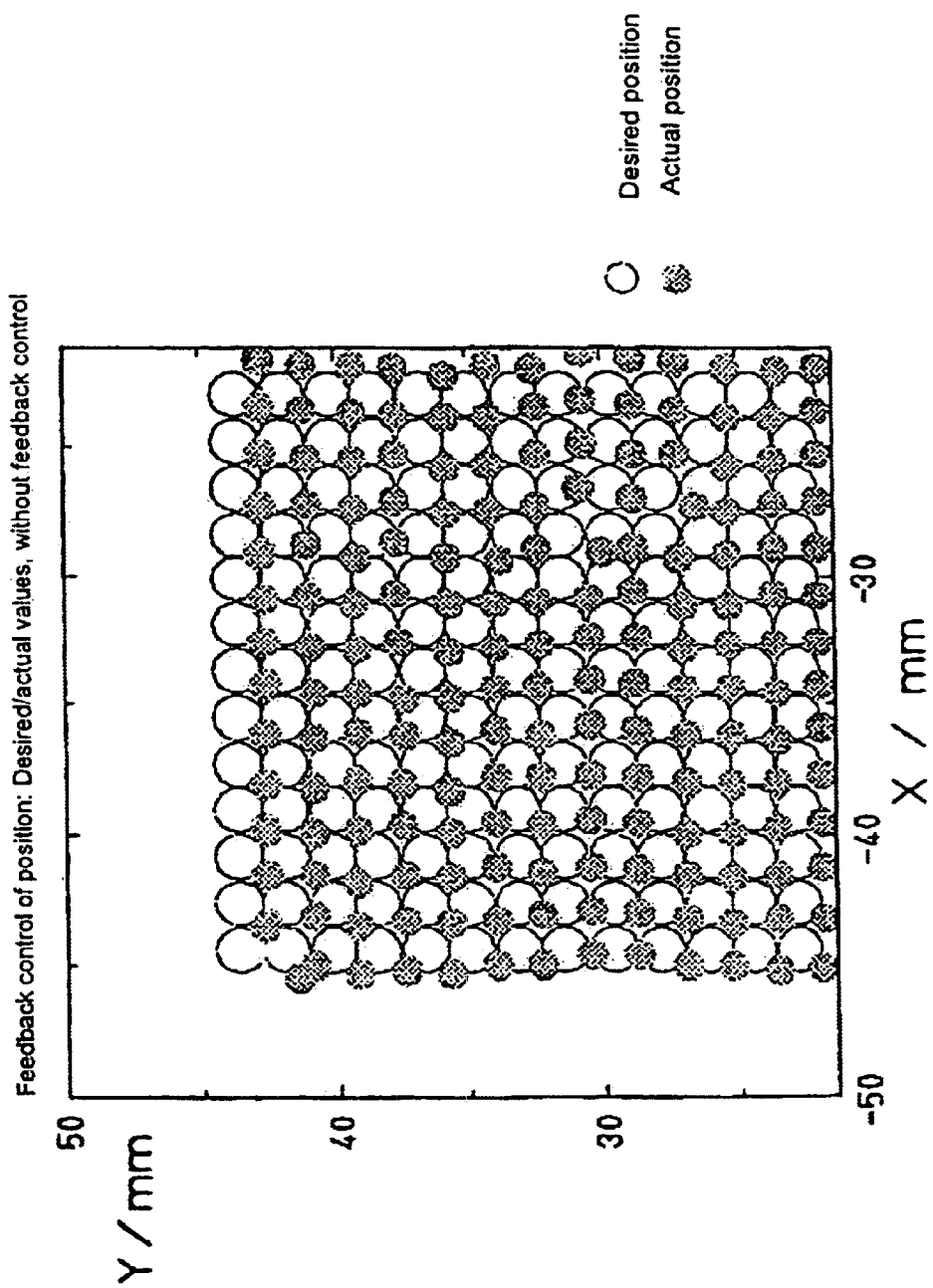
FIG. 4a shows a further desired position/actual position comparison of an ion therapy beam before switching on an apparatus according to the invention.

FIG. 4a shows a further desired value/actual value position comparison of an ion therapy beam before switching on an apparatus according to the invention for the feedback control of a grid scanner. The ordinate in the vertical Y direction and the abscissa in the horizontal X direction are again measured in millimetres from the isocentre. As can be clearly seen, a larger area of 90×90 mm is scanned, compared with the diagram in FIG. 3a, which has 75×75 mm and, in addition, the beam position density is significantly increased compared with the diagram in FIG. 2A so that overall, with 2,116 beam positions, there is almost a doubling of beam positions. In the case of this diagram also, it is assumed that, without the feedback control according to the invention, the beam position is matched at the isocentre within the predetermined and permissible ranges for the actual position. As can be clearly seen, when the positional feedback control according to the invention is not used, significant discrepancies between the actual position and desired position come about for the beam positions in the far top left-hand region relative to the isocentre. As already mentioned earlier, by virtue of the doubling of beam positions, the amount of work involved in measuring and drawing up correction tables would double compared to FIG. 3a, if conventional technology were used. As a result of the grid scanner feedback control according to the invention, that amount of work can be significantly reduced.

Figure 4B:
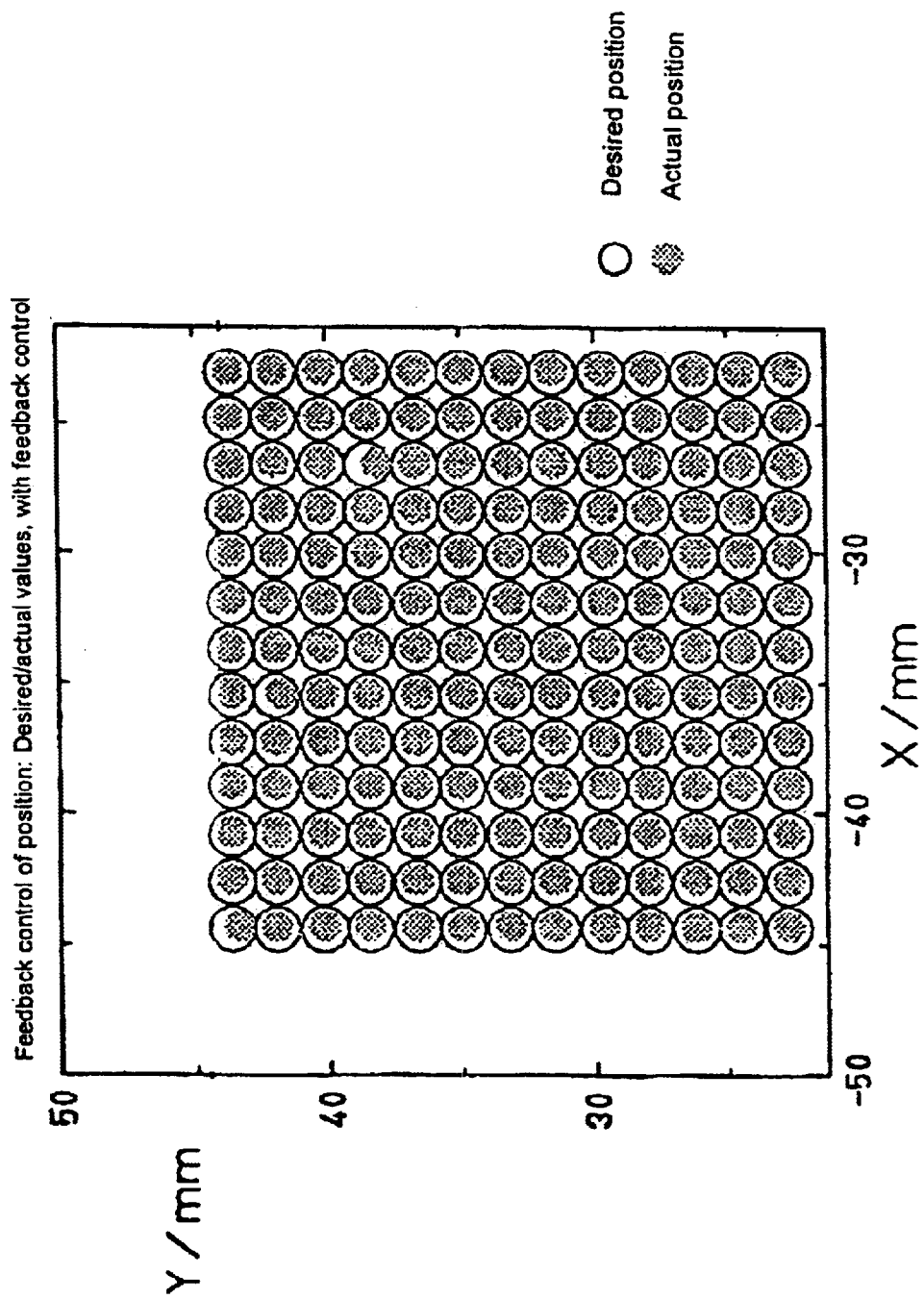
FIG. 4b shows a desired position/actual position comparison of FIG. 4a after switching on the apparatus for feedback control of the position from measurement cycle to measurement cycle according to a further embodiment of the invention.

FIG. 4b, on the other hand, shows a desired value/actual position comparison of FIG. 4a after switching on the apparatus for the feedback control of the position of the ion therapy beam from measurement cycle to measurement cycle according to a further embodiment of the invention. Because the measurement cycle duration can be significantly shortened compared to the duration for which an ion beam must be held in a beam position in order to allow a pre-calculated dose to act in that position on pathological tumour tissue, a number of feedback control cycles are possible for realignment of the ion beam in a beam position so that the actual position can be brought very precisely into concordance with the desired position during the irradiation duration of a beam position. That is made clear by the result shown in FIG. 4b.

The millimetre divisions on the ordinate for vertical deflection in the Y direction and for horizontal deflection in the X direction are identical in this case to the diagram in FIG. 4a, as are the number and position of the shown desired positions for the beam position. The actual positions of the beam lie completely within the planned desired positions after realignment from measurement cycle to measurement cycle. For that purpose, the real-time software in the control and read-out module (SAMO1) for the location-sensitive detector calculates the actual value of the beam position from the detector raw data for each measurement cycle and sends that information to the control and read-out module (SAMS) for the beam magnets and magnet current supply devices (MGN) by way of the data connection of the two control and read-out modules. For each feedback control cycle, which may be either a measurement cycle of location measurement or a cycle from beam position to beam position, the real-time software in the control and read-out module (SAMS) for the scanner magnets then compares the desired position and the actual position and calculates current-correction values for the horizontal and vertical magnet power supply units (MGN) of the grid scanner and then sets the corrected current values, which result in an improved magnetic field setting in the scanner magnets and, as a result, improve the beam position.

In order to avoid feedback control oscillations, realignment of the beam position can be carried out in damped manner; furthermore, upper thresholds can be fixed in order to limit the correction—which is extremely desirable in an application where safety is as relevant as it is in ion beam therapy. In order to obtain the improvement of the result of FIG. 4b compared to the result shown in FIG. 3b, the duration of a measurement cycle can be up to two orders of magnitude smaller than the duration of irradiation of a beam position, as a result of which the feedback control accuracy can be increased because it is furthermore possible also to compensate for higher-frequency beam position variations.

What is claimed is:

1. Apparatus for the feedback control of a grid scanner in ion beam therapy, which has, at least, the following devices:
   scanner magnet current supply devices (MGN) for ion beam scanner magnets that deflect horizontally (X) and vertically (Y) with respect to the middle of the ion beam, the supply devices (MGN) being controlled by control and read-out modules (SAMS) for the scanner magnets,
   a location-sensitive detector (MWPC1) for location measurement, which is controlled by means of a control and read-out module (SAMO1),
   a sequence control device (VMEAS), which controls the activation and read-out sequence among the devices of the apparatus,
   characterized in that the apparatus
   has in the sequence control device (VMEAS) a circuit arrangement having a feedback loop between the control and read-out modules (SAMS) for the scanner magnets and the control and read-out module (SAMO1) of the location-sensitive detector (MWPC1) and,
   in circuitry and sequence, the control and read-out modules (SAMS) for the scanner magnets and the control and read-out module (SAMO1) of the location-sensitive detector (MWPC1) in the sequence control device (VMEAS) are technically so arranged that the control and read-out modules (SAMS) for the scanner magnets are arranged serially after the control and read-out module (SAMO1) of the location-sensitive detector (MWPC1).

2. Apparatus according to claim 1, characterized in that a multi-wire proportional chamber is used as the location-sensitive detector (MWPC1).

3. Apparatus according to claim 1 characterized in that it has at least one ionization chamber (IC1) for measuring the intensity of the ion beam, the control and read-out module (SAMI1) of which ionization chamber is, within the sequence control (VMEAS), technically arranged, in circuitry and sequence, before the control and read-out module (SAMO1) of the location-sensitive detector (MWPC1).

4. Method for the feedback control of a grid scanner in ion beam therapy, wherein the grid scanner has, at least, the following devices:
   scanner magnet current supply devices (MGN) for ion beam scanner magnets that deflect horizontally (X) and vertically (Y) with respect to the middle of the ion beam, the supply devices (X, Y) being controlled by control and read-out modules (SAMS) for the scanner magnets,
   a location-sensitive detector (MWPC1) for location measurement, which is controlled by means of a control and read-out module (SAMO1),
   a sequence control device (VMEAS), which controls the activation and read-out sequence among the devices of the apparatus, and
   wherein the method is characterized by the following steps:
   comparison of information, deposited in the location measurement control and read-out module (SAMO1) of a supervisory control system and relating to the desired position of the beam plan, with the actual measured position of the beam position from a location-sensitive detector, in real time,
   determination of a correction value for the scanner magnet supply devices (MGN) of the grid scanner, and
   setting the correction value for the horizontal and vertical magnet supply devices (X, Y) of the grid scanner and realignment of the beam position.

5. Method according to claim 4, characterized in that the realignment is carried out from beam position to beam position.

6. Method according to claim 4, characterized in that the realignment is carried out from measurement cycle to measurement cycle, the duration of a measurement cycle being shorter than the duration of a beam position.

7. Method according to claim 4, characterized in that, for each measurement cycle, real-time software in the control and read-out module (SAMO1) of the location-sensitive detector (MWPC1) calculates the actual value of the beam position from the detector data and sends that information by way of a data connection between the control and read-out module (SAMO1) of the location-sensitive detector (MWPC1) and the control and read-out modules (SAMS) for the scanner magnets.

8. Method according to claim 4, characterized in that, for a feedback control cycle, real-time software compares the desired position and the actual position of the beam position and calculates current-correction values for the horizontal and vertical magnet current supply device (GMN) of the grid scanner and sets the corrected current values.

9. Method according to claim 4, characterized in that beam realignment is carried out using damping that is arranged to be set by means of the real-time software in the control and read-out modules for the control magnet (SAMS).

10. Method according to claim 4, characterized in that rapid switching-off of the beam is triggered by the control and trigger module (SAMO1) of the location-sensitive detector in real time if the difference between the measured value and the desired value of the beam position exceeds a threshold that is arranged to be set in the real-time software of the control and read-out module (SAMO1) of the location-sensitive detector (MWPC1).

* * * * *